US00PP29143P3

(12) United States Plant Patent
Doguet et al.

(10) Patent No.: US PP29,143 P3
(45) Date of Patent: Mar. 20, 2018

(54) ZOYSIAGRASS PLANT NAMED 'M60'

(50) Latin Name: ***Zoysia matrella* (L.) Merr.**
Varietal Denomination: M60

(71) Applicants: David Doguet, Pleasanton, TX (US); Daric Alan Doguet, Jourdanton, TX (US); Virginia Gail Lehman, Lebanon, OR (US)

(72) Inventors: David Doguet, Pleasanton, TX (US); Daric Alan Doguet, Jourdanton, TX (US); Virginia Gail Lehman, Lebanon, OR (US)

( * ) Notice: Subject to any disclaimer, the term of this patent is extended or adjusted under 35 U.S.C. 154(b) by 58 days.

(21) Appl. No.: 14/999,527

(22) Filed: May 20, 2016

(65) Prior Publication Data

US 2017/0339816 P1 Nov. 23, 2017

(51) Int. Cl.
*A01H 5/12* (2006.01)

(52) U.S. Cl.
USPC ..... Plt./390
CPC ..... *A01H 5/12* (2013.01)

(58) Field of Classification Search
USPC ..... Plt./390
See application file for complete search history.

(56) References Cited

U.S. PATENT DOCUMENTS

| | | | |
|---|---|---|---|
| PP10,636 | P | 10/1998 | Engelke |
| PP11,515 | P | 9/2000 | Engelke |
| PP13,166 | P2 | 11/2002 | Doguet |
| PP13,178 | P2 | 11/2002 | Doguet |
| PP14,130 | P2 | 9/2003 | Engelke |
| PP17,808 | P2 | 6/2007 | Doguet |
| PP17,824 | P2 | 6/2007 | Doguet |
| PP25,203 | P3 | 12/2014 | Doguet |

*Primary Examiner* — Annette H Para

(57) ABSTRACT

An asexually reproduced variety of perennial zoysiagrass with a unique combination of morphological characters including fine leaf blade width and medium green color.

2 Drawing Sheets

Latin name of the genus and species of the plant claimed: The present invention relates to the genus and species *Zoysia matrella* (L.) Merr.

Variety denomination: 'M60'.

CROSS-REFERENCE TO RELATED APPLICATIONS

"Not Applicable"

STATEMENT REGARDING FEDERALLY SPONSORED RESEARCH OR DEVELOPMENT

"Not Applicable"

BACKGROUND OF THE INVENTION

Field of Invention

The present invention relates to a new and distinct asexually reproduced variety of perennial zoysiagrass (*Zoysia matrella* (L.)) Merr.

BRIEF SUMMARY OF THE INVENTION

This invention relates to a new and distinct perennial zoysiagrass cultivar identified as 'M60' zoysiagrass (herein referred to as 'M60'). The inventors, David L. Doguet, Daric Doguet, and Virginia G. Lehman, discovered 'M60' under cultivated conditions near Poteet, Tex. in a collection of seedling plants. The seedling plants originated from proximity crosses among 'Zeon' (U.S. Plant Pat. No. 13,166), 'L1F' (U.S. Plant Pat. No. 25,203), '29-2 B9' (unpatented), and '380-1' (unpatented). 'M60' was identified in 2011 as a distinctly different vegetative patch or clonal plant differing from the surrounding plants. 'M60' showed a fine leaf texture, with a dark green color, both finer and darker than 'Zeon' (U.S. Plant Pat. No. 13,166). The inventors asexually reproduced 'M60' by taking vegetative cuttings of stolons and rhizomes, cutting the rhizomes and stolons into segments, each with a vegetative bud, and rooting them in potting media. 'M60' zoysiagrass will be used as a turfgrass suitable for home lawns, sports fields, and golf course greens and tees.

For purposes of registration under the "International Convention for the Protection of New Varieties of Plants" (generally known by its French acronym as the UPOV Convention) and noting Section 1612 of the Manual of Plant Examining Procedure, it is proposed that the title of the invention is Zoysiagrass plant named 'M60'.

BRIEF DESCRIPTIONS OF THE ILLUSTRATIONS

FIG. 1. Tiller of 'M60' zoysiagrass.
FIG. 2. Inflorescence of 'M60' zoysiagrass.

COMPLETE BOTANICAL DESCRIPTION OF THE VARIETY

'M60' was characterized in greenhouse and field conditions. 'M60' is a unique variety of zoysiagrass (*Zoysia matrella* (L.)) Merr. that was discovered under cultivated conditions. The inventors, David L. Doguet, Daric Doguet, and Virginia G. Lehman, discovered 'M60' under cultivated conditions near Poteet, Tex. in a collection of seedling plants. The seedling plants originated from proximity crosses among 'Zeon' (U.S. Plant Pat. No. 13,166), 'L1F' (U.S. Plant Pat. No. 25,203), '29-2 B9' (unpatented), and '380-1' (unpatented). Both unpatented plants originated from field grown open pollinated crosses between 'VJay' (unpatented), '6136' (U.S. Plant Pat. No. 17,808), and 'JaMur' (U.S. Plant Pat. No. 13,178) *zoysia* plants. The seed was combined from the four parents, each individual seed was planted in a pot, and plants from the seed were subsequently transplanted to the field. 'M60' was identified in 2011 as a distinctly different vegetative patch or clonal plant. 'M60' differed from the surrounding plants in a fine leaf texture and darker green color than 'Zeon' (U.S. Plant Pat. No. 13,166). In the plantings near Poteet, Tex., 'M60' showed a much finer leaf than both potential parents '29-2-B9' or '380-1'. The plants were located in USDA Plant Hardiness Zone 8. The inventors asexually reproduced 'M60' in both Poteet, Tex. and Lebanon, Oreg. by taking vegetative cuttings of stolons and rhizomes, cutting the rhizomes and stolons into segments, each with a vegetative bud, and rooting them in potting media. Planting of the rooted material provided planting stock for studying performance and for comparison of morphological characters after propagation. 'M60' has been propagated by rhizomes, stolons, tillers, and sod. Asexually reproduced plants of 'M60' have remained stable and true to type through successive generations of propagation. No seedling establishment from 'M60' has been noticed in either greenhouse or field studies.

'M60' is a perennial zoysiagrass that spreads by both stolons and rhizomes. Characteristics of 'M60' measured in 2015 and 2017 were taken from plants that were approximately 12 months in age. The greenhouse was located near Lebanon, Oreg., with a nighttime low temperature of 50 degrees F., and daytime high of 80 degrees F., and a minimum soil temperature of 77 degrees F. The plants were grown under natural daylength without supplemental lighting. The plants were fertilized with the equivalent of 1 pound of actual N per month, using a soluble fertilizer of 20-20-20 in four equal soluble applications per month.

'M60' has a fine leaf texture, with a leaf width not significantly different from 'Diamond' (Table 1). 'M60' has finer leaf than both potential parents '29-2-B9' or '380-1', Zeon, L1F, or 'M66' (Table 4). 'M60' has sparse to absent leaf hairs except for a very few long hairs (1.5 mm length) versus 'Zorro', which has many leaf surface hairs (Table 2). 'M60' has a thicker youngest stolon node and 1-2 stolon internode lengths not different from 'Diamond' (Table 3). 'M60' shows lighter green color than 'L1F' when maintained in turf plots mowed at greens height (Table 6).

'M60' has shown moderate resistance to brown patch when grown in California. 'M60' rated a 1.1 (where 9-heavy disease symptoms) when 'Zorro' rated a 1.8; 'L1f' rated a 2.7; 'Zeon' rated a 6.3; 'Palisades' rated 1.5, all with a lsd (p=0.05) of 1.3. In addition, in greenhouse conditions, 'M60' has shown susceptibility to *zoysia* rust (*Puccinia* species).

'M60' has not shown susceptibility to the zoysiagrass mite when tested at Poteet, Tex., where susceptible varieties have shown the coachwhip leaf symptoms of the mite. 'M60' has shown good turfgrass performance and temperature adaptation when tested as far north as Athens, Ga., USDA hardiness zone 8a, which would extend the area of adaptation for 'M60' in a line from northern Georgia across central Texas in an East/West line and on a North/South line from Atlanta, south through Mexico. 'M60' will be limited only by winter survival in colder regions, and has shown less winter survival than 'L1F' when tested in turf plots near Lebanon, Oreg. 'M60' is similar to most fine textured zoysiagrasses in water use demands as shown in test situations near Poteet, Tex., 'M60' is adapted from sandy to heavier loam soil textures and from slightly acid to slightly alkaline soil pH.

TABLE 1

Leaf blade widths and lengths and texture class of selected zoysiagrass cultivars, measured under greenhouse conditions in Lebanon, OR, 2015.

| Variety | Length, 2nd youngest crown leaf -cm- | Width, 2nd youngest crown leaf -mm- | Leaf Texture Class Rating |
|---|---|---|---|
| 'M60' | 2.1 | 1.6 | Fine |
| 'Zorro' | 2.33 | 1.76 | Medium |
| 'M66' | 1.60 | 1.96 | Medium-fine |
| 'Diamond' | 2.51 | 1.3 | Fine |
| 'Y2' | 3.3 | 2.76 | Medium-coarse |
| Lsd, p = 0.05 | 0.9 | 0.39 | |

TABLE 2

Adaxial leaf hair presence or absence of selected zoysiagrass cultivars, measured under greenhouse conditions in Lebanon, OR, 2015.

| Variety | Leaf hair, adaxial Presence/ Number |
|---|---|
| 'M60' | Sparse |
| 'M66' | Sparse |
| 'Diamond' | Absent |
| 'Zorro' | Many |

TABLE 3

Stolon characters of selected zoysiagrass cultivars, measured under greenhouse conditions in Lebanon, OR, 2015.

| Variety | Thickness 1st youngest stolon node -mm- | Thickness 2nd youngest stolon node -mm- | Stolon Internode length, 1st to 2nd node -cm- | Stolon Internode length, 2nd to 3rd node -cm- | Stolon Internode length, 3rd to 4th node -cm- |
|---|---|---|---|---|---|
| 'M60' | 1.75 | 1.62 | 1.4 | 1.57 | 1.57 |
| 'Zorro' | 1.83 | 1.67 | 2.67 | 2.9 | 2.53 |
| 'M66' | 1.72 | 1.53 | 1.1 | 1.43 | 1.03 |
| 'Diamond' | 1.11 | 1.28 | 1.26 | 1 | 0.93 |
| 'Y2' | 2.4 | 2.37 | 2.47 | 2.57 | 2.07 |
| Lsd, p = 0.05 | 0.56 | 0.57 | 0.61 | 0.92 | 0.94 |

TABLE 4

Leaf characters of selected zoysiagrass cultivars, measured under greenhouse conditions in Lebanon, OR, 2017.

| Variety | Length, 2nd youngest crown leaf -cm- | Width, 2nd youngest crown leaf -mm- |
|---|---|---|
| 'M60' | 2.4 | 1.1 |
| 'M66' | 3.8 | 1.58 |
| 'L1f' | 3.6 | 1.16 |
| 'Zeon' | 5.6 | 1.56 |
| '29-2 B9' | 4.6 | 2.18 |
| '380-1' | 3.3 | 2.67 |
| Lsd, p = 0.05 | 1.3 | 0.48 |

TABLE 5

Stolon characters of selected zoysiagrass cultivars, measured under greenhouse conditions in Lebanon, OR, 2017.

| Variety | Thickness 1st youngest stolon node -mm- | Thickness 2nd youngest stolon node -mm- | Stolon Internode length, 1st to 2nd node -cm- | Stolon Internode length, 2nd to 3rd node -cm- | Stolon Internode length, 3rd to 4th node -cm- |
|---|---|---|---|---|---|
| 'M60' | 1.43 | 1.43 | 0.89 | 0.81 | 0.75 |
| 'M66' | 1.63 | 1.63 | 0.83 | 0.93 | 0.68 |
| 'Zeon' | 1.40 | 1.45 | 07.2 | 0.98 | 0.8.0 |
| '29-2 B9' | 2.0 | 2.4 | 0.90 | 0.85 | 1.16 |
| 'L1F' | 1.63 | 1.56 | 0.77 | 1.08 | 0.95 |
| '380-1' | 1.6 | 1.3 | 1.76 | 1.6 | 1.3 |
| Lsd, p = 0.05 | 0.42 | 0.56 | 0.49 | 0.51 | 0.49 |

TABLE 6

Turf quality ratings taken in August in Poteet, TX in 2014, with turf mowed at greens heights.

| Variety | Uniformity ^^ | Quality # | Texture $ | Color ^ |
|---|---|---|---|---|
| 'M60' | 7.0 | 5.5 | 6.3 | 6.3 |
| 'Diamond' | 7.7 | 6.8 | 7.3 | 7.2 |
| 'M85' | 7.0 | 4.7 | 7.5 | 6.2 |
| 'L1F' | 7.0 | 5.5 | 8.3 | 8.3 |
| CV | 7.8 | 9.08 | 4.6 | 6.0 |
| Lsd, p= 0.05 | 0.9 | 0.81 | 0.56 | 0.69 |

^^ Uniformity rated on a scale of 1-9, 9 = most uniform.
Quality rated on a scale of 1-9, 9 = best quality.
$ Texture rated on a scale of 1-9, 9 = finest texture.
^ Color rated on a scale of 1-9, 9 = darkest green.

TABLE 7

Relative shoot dry weight in response to salt treatment, 2016.

| | |
|---|---|
| 'M60' | 0.68a-d* |
| 'M66' | 0.92a |
| 'Diamond' | 0.4cde |
| 'L1f' | 0.54bcde |
| 'Zeon' | 0.58bcde |
| 'Zorro' | 0.3de |

*Means followed by the same letter are not significantly different (p <= 0.05) as determined by Tukey HSD pairwise comparison test.
Plants were grown with sub-irrigation with 300 mM NaCl for 8 weeks in a randomized complete block design. Fifteen entries were subjected to the treatment.

TABLE 8

Mean Fall Color*, 2016, California.

| Entry | |
|---|---|
| 'M60' | 1.1 |
| 'M66' | 3 |
| 'M85' | 1.22 |
| 'JaMur' | 5 |
| 'L1f' | 2.67 |
| 'Zorro' | 3.56 |
| 'Palisades' | 3.56 |
| 'Zeon' | 4.78 |
| Lsd, p = 0.05 | 1.63 |

*Rated on a scale of 1-9, 9 = least color retention

COMPLETE BOTANICAL DESCRIPTION OF THE VARIETY

Origin: 'M60' is a cultivar of a single clone discovered under cultivated conditions in a Poteet, Tex. planting of zoysiagrass clones derived from a collection of seedling plants originating from proximity crosses among 'Zeon' (U.S. Plant Pat. No. 13,166), 'L1F' (U.S. Plant Pat. No. 25,203), '29-2 B9' (unpatented), and '380-1' (unpatented). Both unpatented plants originated from field grown open pollinated crosses between 'VJay' (unpatented), '6,136' (U.S. Plant Pat. No. 17,808), and 'JaMur' (U.S. Plant Pat. No. 13,178) *zoysia* plants. The seed was combined from the four parents, each individual seed was planted in a pot, and plants from the seed subsequently transplanted to the field. 'M60' was identified in 2011 as a distinctly different vegetative patch or clonal plant. 'M60' showed a fine leaf texture with a dark green color, both finer and darker than 'Zeon' (U.S. Plant Pat. No. 13,166). In plantings near Poteet, Tex., 'M60' has a finer leaf texture than either potential parent '29-2-B9' or '380-1' or 'Zeon'.

Classification: *Zoysia matrella* (L.) Merr.

Growth habit: 'M60' is a perennial plant that spreads by stolons and rhizomes and produces a dense, fine textured turfgrass. The inflorescence of 'M60' is a terminal spike-like raceme, with spikelets on short pedicels.

Leaf blade: Rolled in the bud, flat surface.

Leaf blade pubescence: Sparse to few leaf hairs on the adaxial surface, 1.5 mm long.

Leaf margin pubescence: Barbellate margins. 'Palisades' has some barbellate margin to a small degree, but not as prominent or regular as 'M60'.

Leaf sheath pubescence: Absent except for long hairs at mouth of sheath, 1.2 to 2.5 mm in length; 'LR1' mean length sheath mouth hairs: 1.7 mm; Diamond 1.0 mm.

Leaf sheath stem attachment: Ring of short hairs are present inside the sheath where it attaches to the stem, 0.2 mm in length.

Leaf blade margin: 'M60'=slight roughness.

Leaf blade veins: Prominent under 10× magnification.

Leaf blade flexibility (softness): Medium stiff.

Vegetative leaf, 2nd youngest vegetative leaf:

*Blade length range.*—'M60': 2.0 cm to 2.1 cm, mean length: 2.1 cm.

*Blade width mean.*—'M60': 1.5 mm to 1.9 mm, mean width: 1.7 mm; 'Zorro' mean width: 1.76 mm; 'Diamond' mean width: 1.3 mm.

Sheath length, 4th youngest vegetative leaf: Mean length 'M60': 1.6 cm.

Inflorescence characters:

*Culm total length, including floral area to node below flag leaf.*—2.3 cm. Length of stem of inflorescence: 1.7 cm. Floral area length: 0.6 cm.

*Culm width, stem thickness, base of floral area.*—0.55 mm.

*Anther length.*—0.75 mm.

*Floret* (*seed*) length.—2.3 mm.

*Floret* (*seed*) width.—1.12 mm.

*Node thickness, node below flag leaf.*—0.75 mm.

*Pedicel length.*—1.76 mm.

*Flag leaf length.*—'M60': 0.65 cm.

*Flag leaf width.*—'M60': 1.5 mm.

Mature plant height, including inflorescence: 5.0 to 6.0 with a mean of 5.5 cm.

Color notations, vegetative characters, based on The R.H.S. Colour Chart (light quality, photoperiod, and general growth of the plants affect color notations):

*Leaf blade color adaxial leaf surface.*—137C green.

*Leaf blade color abaxial leaf surface.*—137C green.

*Stolon color, in absence of light.*—158B yellow-white to 159B orange-white.

Color notations, floral characters, based on The R.H.S. Colour Chart (light quality, photoperiod, and general growth of the plants affect color notations):

*Culm stalk.*—144A yellow-green.

*Stigma.*—158D greyed yellow-white.

*Anther color, fresh.*—154C yellow-green with 187A greyed purple.

Turf color (rated 1-9, 9 best), mowed at greens height: 'M60': 6.3; 'Diamond': 7.2.

Turf quality (rated 1-9, 9 best), mowed at greens height: 'M60': 5.5; 'Diamond': 6.8.

REFERENCES CITED

U.S. Patent Documents

| | | |
|---|---|---|
| November 2002 | Doguet, D. | U.S. PP 13,166 'Zeon' zoysiagrass |
| November 2002 | Doguet, D. | U.S. PP 13,178 'JaMur' zoysiagrass |
| June 2007 | Doguet, D. | U.S. PP 17,808 '6136' zoysiagrass |
| June2007 | Doguet, D. | U.S. PP 17,82 'Y2' zoysiagrass |
| December 2014 | Doguet, D. | U.S. PP 25,203 'L1f' zoysiagrass |
| October 1998 | Engelke, M.C. | U.S. PP 10,636 'Diamond' zoysiagrass |
| September 2000 | Engelke, M.C. | U.S. PP 11,515 'Palisades' zoysiagrass |
| July 2002 | Engelke, M.C. | U.S. PP 14,13 'Zorro' zoysiagrass |

We claim:

1. A new and distinct variety of zoysiagrass plant, substantially as described and illustrated herein, characterized particularly by a unique combination of morphological characters.

* * * * *

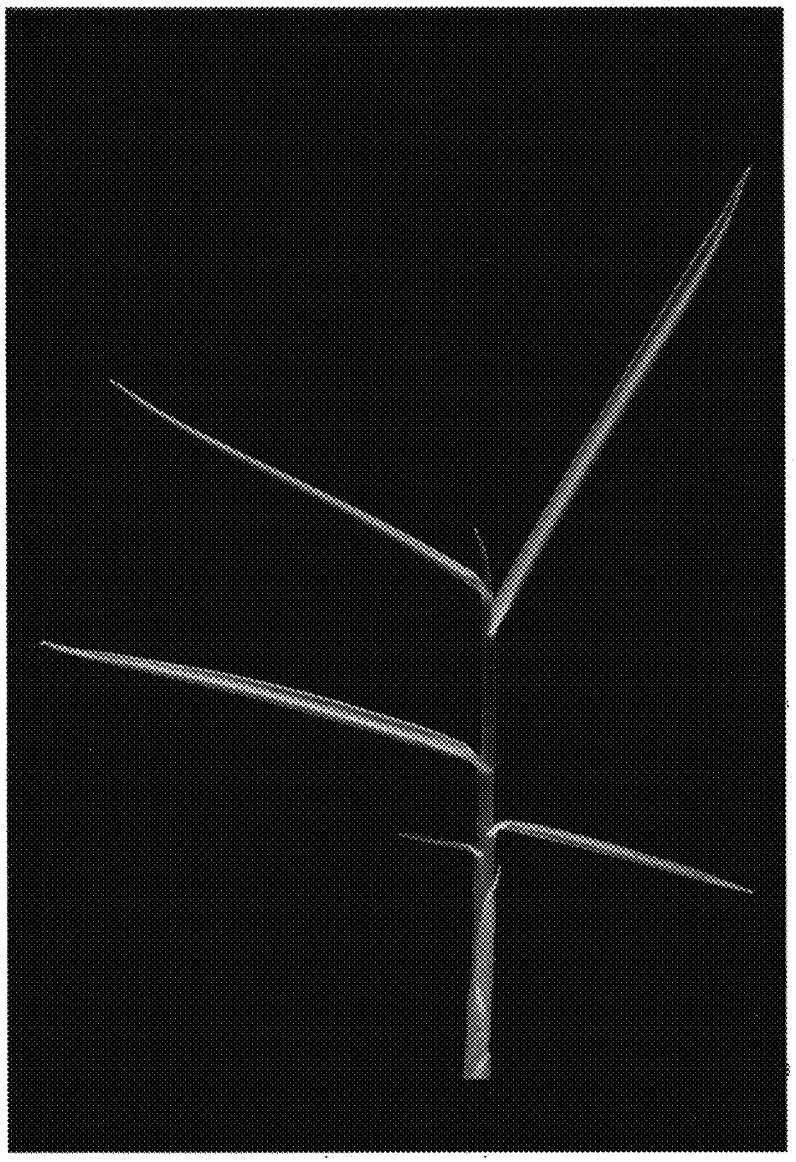
Figure 1. Tiller of 'M60' zoysiagrass.

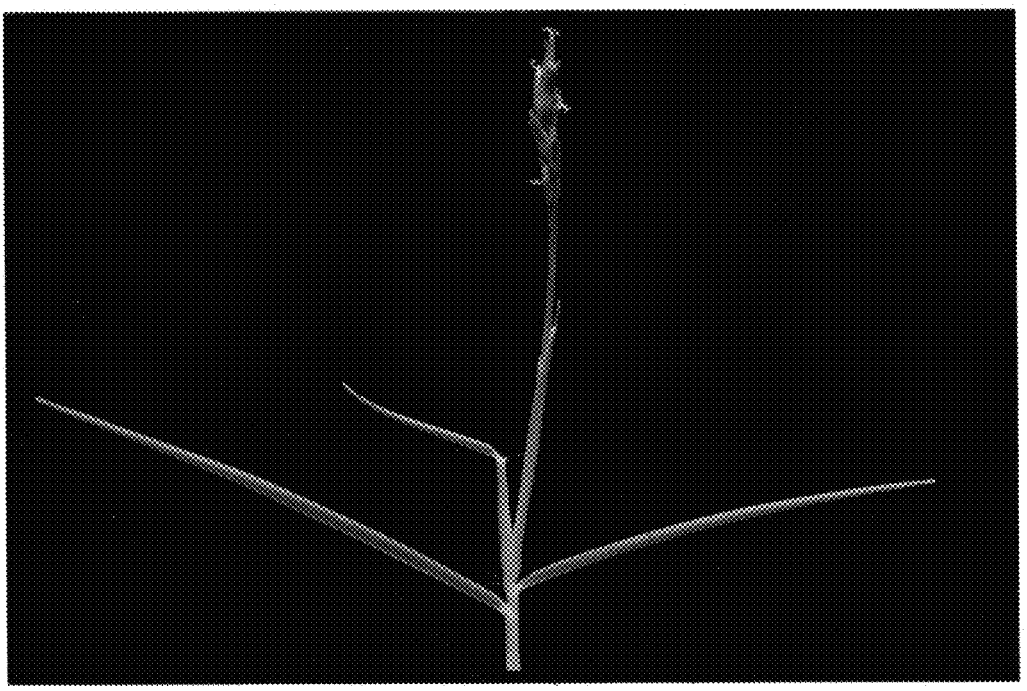
Figure 2. Inflorescence of 'M60' zoysiagrass.